United States Patent [19]
Eschwey et al.

[11] Patent Number: 6,134,914
[45] Date of Patent: Oct. 24, 2000

[54] ON-LINE RECOVERY OF XENON FROM ANAESTHETIC GAS

[75] Inventors: Manfred Eschwey, Duesseldorf; Reiner Hamm, Neukirchen-Vluyn; Peter Neu; Renate Schmidt, both of Duisburg; Georg Schroeder, Bochum, all of Germany

[73] Assignee: Messer Griesheim GmbH, Germany

[21] Appl. No.: 09/242,952

[22] PCT Filed: Jul. 19, 1997

[86] PCT No.: PCT/EP97/03885

§ 371 Date: Nov. 15, 1999

§ 102(e) Date: Nov. 15, 1999

[87] PCT Pub. No.: WO98/08583

PCT Pub. Date: Mar. 5, 1998

[30] Foreign Application Priority Data

Aug. 30, 1996 [DE] Germany .................. 196 35 002

[51] Int. Cl.$^7$ ...................................... F25J 1/00
[52] U.S. Cl. ................................. 62/637; 62/925
[58] Field of Search ......................... 62/637, 925

[56] References Cited

U.S. PATENT DOCUMENTS

| | | | |
|---|---|---|---|
| 3,853,507 | 12/1974 | Monroe et al. | 55/269 |
| 4,668,261 | 5/1987 | Chatzipros et al. | 62/55.5 |
| 4,755,201 | 7/1988 | Eschwey et al. | 62/637 |
| 5,520,169 | 5/1996 | Georgieff et al. | 128/204.16 |
| 5,626,035 | 5/1997 | Pozvonkov | 62/637 |

FOREIGN PATENT DOCUMENTS 44 11 533  4/1994  Germany .

*Primary Examiner*—Ronald Capossela
*Attorney, Agent, or Firm*—Connolly Bove Lodge & Hutz LLP

[57] ABSTRACT

A process is disclosed for separating a component from a gaseous mixture, in particular for separating xenon from the breathing gas exhaled by an anaesthetized patient. The disclosed process has the following steps: the gaseous mixture is brought into contact with a cooling surface at a temperature below the melting point of the components to be separated, the proportion of the gaseous mixture which is not condensed on the cooling surface in a solid state is carried away, and the component condensed on the cooling surface is heated above the melting point of the component to be separated. Also disclosed are a device for carrying out this process, a corresponding process for recovering anaesthetic gas and an associated anaesthetic equipment.

11 Claims, 2 Drawing Sheets

ON-LINE RECOVERY OF XENON FROM ANAESTHETIC GAS

BACKGROUND OF THE INVENTION

The invention relates to a process and a device for separating off one component from a gas mixture and to a process for recycling a gas mixture such as an anesthetic gas. The invention finds application, in particular, in connection with instruments for and techniques of xenon anesthesia.

The anesthetic effects of xenon have been known since the 1940s. A mixture of about 80% xenon and 20% oxygen is regarded as a virtually ideal anesthetic gas, with numerous advantages over the anesthetic gases predominantly in use today which are based on laughing gas. Owing to the high costs of xenon, xenon anesthesia is practiced hardly at all in the clinical field. In order to reduce these costs proposals have therefore been made, for example in DE 44 11 533 C1, for anesthetic machines having a xenon recovery system. In the case of the recovery system proposed in DE 44 11 533 C1, the exhaled respiratory gas is first cleaned and then compressed and passed into a pressure vessel which is taken into a cooling device. By means of the cooling device the pressure vessel is cooled to such an extent that the xenon that is to be recovered is liquefied. The gaseous constituents in the pressure vessel are let off through an outflow valve. When there is a sufficient amount of liquid xenon in the pressure vessel, it is pumped into a further vessel.

This device has the disadvantage of a highly complex apparatus for compressing the gas and for the cooling of an entire vessel. Moreover, the degree of transfer in xenon recovery is not satisfactory.

DE 35 18 283 A1 discloses a process for removing volatile purities from gases which are produced in the semiconductor industry, where the gas to be cleaned is guided, in a vacuum system, onto a cold surface of a condensor, on which condenser the gas to be purified is deposited while the more volatile impurities are drawn off continuously in gas form from the vacuum system. In this process too, the vacuum system used means that the apparatus for recovery is highly complex.

SUMMARY OF INVENTION

It is the object of the invention to provide a simple and economic process for separating off one component of an anesthetic gas from the expirational respiratory gas of an anesthetized patient, and an associated device. Another object of the invention is to provide an economic recycling process for an anesthetic gas, especially for a xenon-based anesthetic gas.

It has surprisingly been found that it is also still possible to separate off xenon with an acceptable purity with condensation under a pressure in the range from 0.6 bar to 150 bar. When the novel recycling process is used for an anesthetic gas, it is even possible to reduce the purity requirements for the xenon still further, since residual fractions of oxygen in the recovered xenon can be compensated for by an appropriately lower proportion of oxygen when the anesthetic gas is remixed.

Advantageously, through the use of a heat exchanger consisting of a tube or a tube bundle, the energy required to condense out the xenon is reduced, since it is now necessary to cool no longer the entire vessel but instead a comparatively small condensation surface to the temperature which is required for the condensation of the xenon in solid form. At the same time this opens up a possibility of controlling the layer thickness. Since the solid xenon deposited on the heat exchanger has an insulating effect, the degree of cooling of the interior of the vessel by the heat exchanger drops as the thickness of the solid xenon layer grows, so that the thickness of the xenon layer on the heat exchanger can be deduced from the temperature in the vessel.

The pressure produced when the deposited xenon is evaporated can be used, in accordance with the invention, to transfer the recovered xenon to another vessel. Pumps for conveying the recovered xenon for further processing, therefore, can be omitted or made smaller.

The novel process can be designed as a continuous process at low pressure, with the respiratory gas, after first being cleaned, flowing along a tube bundle heat exchanger. The tube bundles of this heat exchanger are advantageously configured such that the flow path along the cooled tubes is as long as possible. The pressure of the gas flowing through the deposition apparatus is in this case typically in the range from 0.6 bar to 5 bar, preferably close to atmospheric pressure.

In accordance with the invention the respiratory gas can also be stored in a pressure vessel in which, after a sufficient amount of gas has flowed in, the xenon is condensed out in solid form on a heat exchanger and the uncondensed gases are let off as overhead gas. In the course of the subsequent evaporation of the xenon deposited in solid form in the sealed vessel, a pressure is brought about which on the one hand enables the separated xenon to be passed into a further vessel, without an additional pump, and on the other hand is also in a range corresponding to the pressure of commercial xenon gas bottles. If, for example, the deposition vessel is designed to a pressure of 150 bar, the pressure which results for the deposited xenon after evaporation is 65 bar. The deposition vessel can therefore be used directly as a store of xenon for further processing.

In accordance with an advantageous embodiment of the invention, two deposition apparatuses are used in tandem. This makes it possible to collect the expirational respiratory gas and to condense out xenon in one of the two deposition apparatuses, while in the other deposition apparatus the xenon already condensed out is evaporated.

The novel process and its modifications are also suitable in principle for separating off a component from a general gas mixture.

Further features and advantages of the invention will become clear from the following detailed description of two exemplary embodiments of the invention in reference to the attached drawings.

THE DRAWINGS

DETAILED DESCRIPTION

Figure 1:
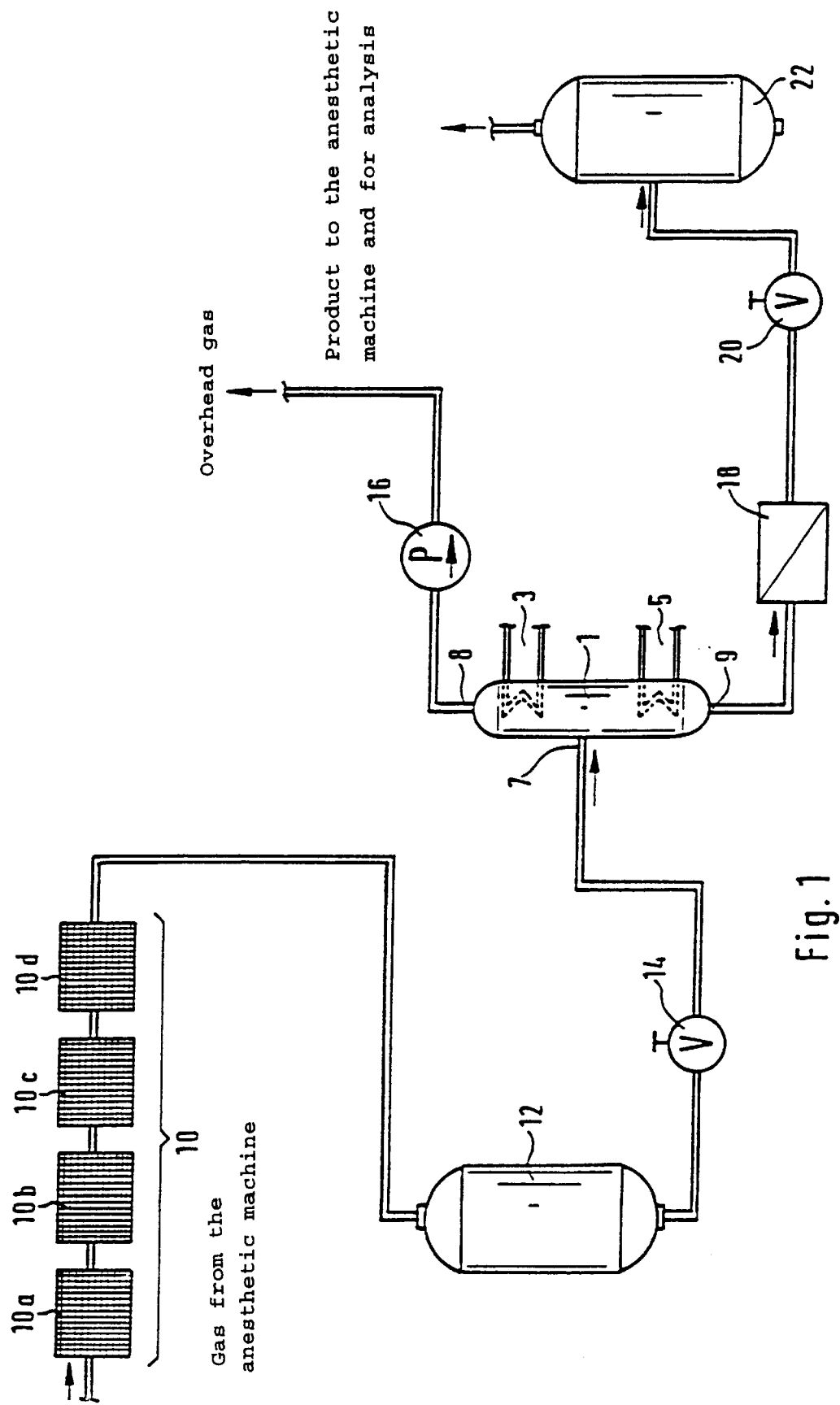
FIG. 1 shows, diagrammatically, a device for recovering xenon from anesthetic gas by a low-pressure process.

FIG. 1 shows a first embodiment of the novel xenon recovery system, in which the xenon is separated off with a low-pressure process. The center of the system is a deposition apparatus 1, which has a heat exchanger 3, which is cooled by liquid nitrogen, and a heater 5, which in the drawing are indicated merely in the form of functional symbols. The deposition apparatus 1 has an inlet 7 for expiration of respiratory gas from an anesthetic machine (not shown) and also two outlets 8 and 9. The heat exchanger 3 consists of a tube bundle through which liquid nitrogen is formed. However, it could also be passed through a surface having good thermal conductivity of a reservoir for liquid nitrogen. The heat exchanger 3 is located in the flow path from the inlet 7 to the outlet 8 and is customarily configured such that as large as possible an area of heat exchanger comes into contact with the gas flow. The heater 5 is an electrical heater which heats the vessel of the deposition apparatus 1.

Interposed between the anesthetic machine and the inlet 7 is an initial cleaning apparatus 10 having four cleaning stages 10a to 10d. The purpose of the four cleaning stages is to remove various impurities present in the expirational respiratory gas from the anesthetic machine. For instance, the cleaning stage 10a can contain soda lime for removing carbon dioxide, the cleaning stage 10b can contain a molecular sieve for removing moisture in the respiratory gas, the cleaning stage 10c can contain an active carbon filter for removing hydrocarbons present as metabolic products in the respiratory gas, and the cleaning stage 10d can contain a particle filter, for example a HEPA filter, for removing suspended particles, microbes and the like. The initial cleaning apparatus 10 is connected to the inlet 7 by way of an intermediate store 12 and a shutoff valve 14.

The first outlet 8 of the deposition apparatus 1 is connected to a membrane pump 16, which passes the gas it sucks in either into the free atmosphere or into a waste-gas collection vessel (not shown). The second outlet is connected by way of a nonreturn valve 18 and a shutoff valve 20 to a collecting vessel 22 for the recovered xenon.

The unit illustrated in FIG. 1 operates as follows: the respiratory gas coming from the anesthetic machine is passed first of all through the initial cleaning apparatus 10, in which impurities such as hydrocarbons and microbes and substances having a higher freezing point than xenon ($H_2O$, $CO_2$) are removed from the gas. The initially cleaned gas is then stored in the intermediate store 12. When the deposition apparatus 1 is ready to receive respiratory gas and/or a sufficient amount of gas has been stored in the intermediate vessel 12, the shutoff valve 14 is opened and the gas flows through the inlet 7 into the deposition apparatus 1. In this arrangement, the pump 16 produces a flow over the heat exchangers 3 whose surface, as a result of cooling by liquid nitrogen, has a temperature of approximately −196° C. On the heat exchange surface of the heat exchanger 3 the xenon (freezing point: −112° C.) is deposited in solid form while the principal impurities, namely oxygen (freezing point −219° C.) and nitrogen (freezing point: −210° C.), remain in gas form and are taken off by suction as overhead gas by the pump 16. Since the components having a higher freezing point than that of xenon have been separated off in the initial cleaning apparatus 10, the xenon deposited on the heat exchanger now contains only very small fractions of impurities.

The deposition process described above is continued there is a sufficient layer thickness of the xenon on the heat exchanger 3. The presence of a sufficient layer thickness can be ascertained, for example, by means of a flow meter in the line to the inlet 7, since a certain amount flowing through corresponds to a certain layer thickness of xenon on the heat exchanger. Another possibility is to detect, by means of a temperature sensor in the vessel of the deposition apparatus, by how much the temperature in the vessel has risen in relation to the start of the deposition process. Since the deposited xenon insulates the heat exchanger 3, a certain layer thickness corresponds to a certain rise in temperature in the vessel of the deposition apparatus 1. When the desired layer thickness is reached, the supply of respiratory gas from the intermediate store 12 is interrupted by means of the valve 14, and the outlet 8 of the deposition apparatus is closed. The vessel of the deposition apparatus 1 is subsequently heated by means of the heater 5 so that the xenon deposited on the heat exchanger 3 is evaporated. As a result there is a buildup of pressure in the vessel of the deposition apparatus 1. Following the evaporation of the xenon, the outlet 9 and the valve 20 are opened, so that the gaseous xenon in the deposition apparatus 1 flows as a result of the built-up pressure into the xenon vessel 22 via the nonreturn valve 18 and the valve 20.

The embodiment described above can be modified in various respects. For instance, the connection between the anesthetic machine and the intermediate store 12 can be designed such that when the valve 14 is closed a moderate pressure, for instance in the range from 3 to 5 bar, is established in the intermediate store. In this case the pump 16 can be omitted and the outlet 8 can be connected directly to the atmosphere. The gas present in the intermediate store 12 then flows, after the valve 14 has been opened, and as a result of the pressure gradient relative to the atmosphere, via the inlet 7 and the outlet 8 through the deposition apparatus 1 and the heat exchanger 3.

Furthermore, the heater can be operated such that after the inlet 7 has been closed the xenon is initially only liquefied, so that impurities included in the solid xenon are released and are removed under suction as overhead gas by the pump 16.

It is also possible to pass the recovered xenon in liquid form to the xenon store 22. In this case, the deposited xenon is only liquefied and a liquid pump is provided in the connection between the outlet 9 and the vessel 22.

Finally, the vessel of the deposition apparatus can also be fitted only with an outlet 8, through which it is possible to lead off both the gas containing impurities, in the course of the deposition process, and, later, the recovered xenon, with a multiway valve passing the emerging gas either into the atmosphere or to the xenon store 22.

Figure 2:
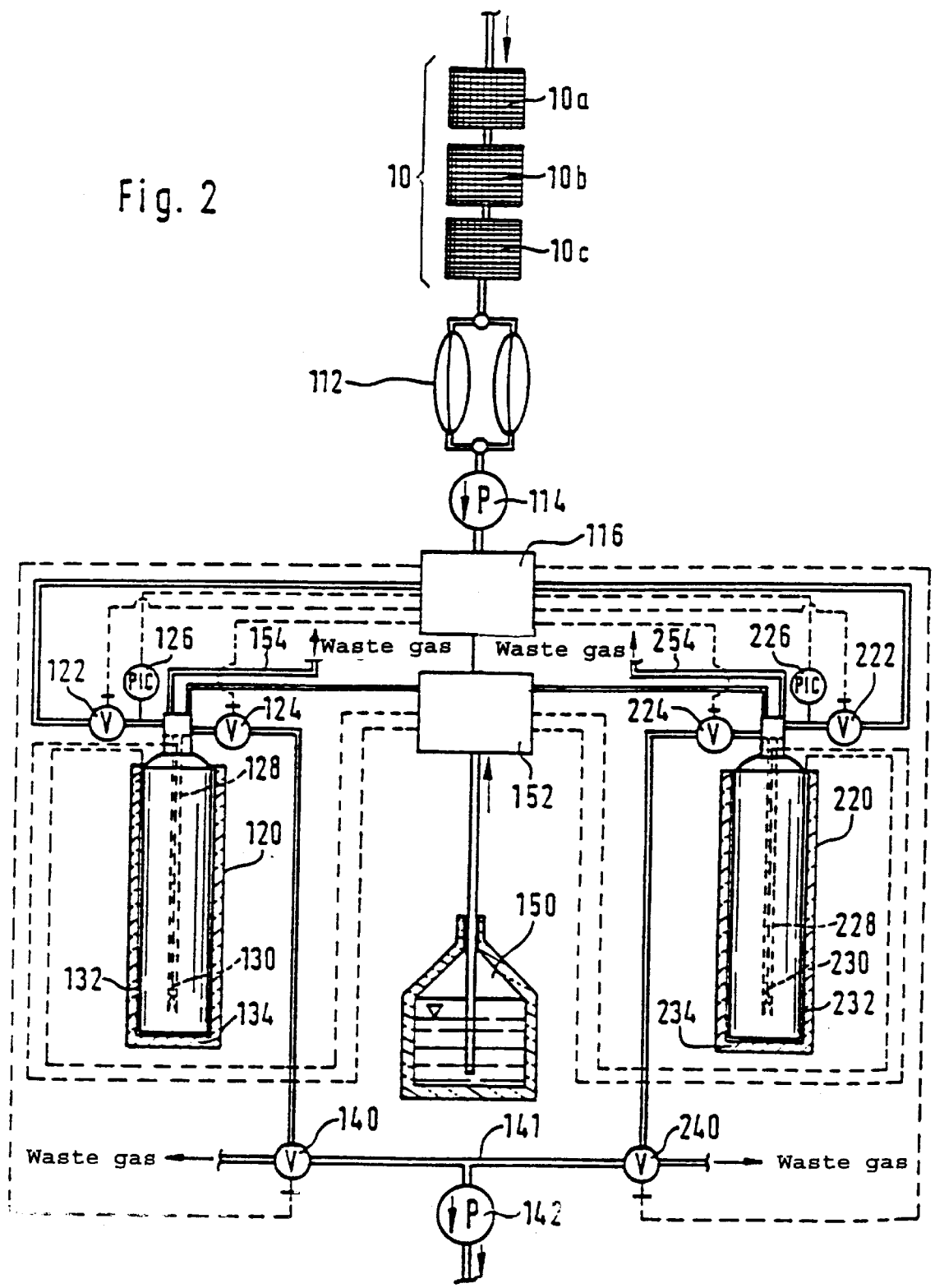
FIG. 2 shows, diagrammatically, a device for recovering xenon by a high-pressure process.

FIG. 2 shows a system for recovering xenon from anesthetic gas in a high-pressure process, where gas lines are shown by solid lines and measurement and control lines (temperature, pressure, pneumatics, flow) are shown by dashed lines. This system again has an initial cleaning apparatus 10 with cleaning stages 10a to 10c for cleaning the expirational respiratory gas coming from the anesthetic machine. The cleaning stages in the initial cleaning apparatus 10 are indicated only by way of example. It is of course also possible here to employ a HEPA filter and/or further cleaning stages. The initial cleaning apparatus 10 is connected by way of a pressureless pump control 112 or buffer with a pump 114 which passes the precleaned respiratory gas via a branch changeover unit 116 to either of two deposition vessels 120, 220, which are identical in construction. The description given below of their construction relates to the first deposition apparatus, with the reference numerals for the second deposition apparatus being indicated in brackets. Each of the two deposition apparatuses consists of a pressure-resistant vessel which is designed for a pressure of 150 bar and has an inlet valve 122 (222) and an outlet valve 124 (224). A pressure sensor 126 (226) detects the pressure in the vessel. In the vessel there is a heat exchanger in the form of a stainless steel cooling tube 128 (228) through which liquid nitrogen can flow. A temperature sensor 130 (230) detects the temperature in the interior of the vessel, while a temperature sensor 132 (232) detects the temperature on the outer wall of the vessel. The vessel itself is surrounded by an insulating jacket 134 (234). The inlet valve 122 (222) is connected via the branch changeover unit 116 to the pump 114, while the outlet valve 124 (224) is connected to a multiway valve 140 (240) which is likewise directed by the branch changeover unit 116. Depending on these directions, the multiway valve 140 (240) leads the gas coming from the outlet valve 124 either off, as waste gas, or via a product line 141 to a pump 142. The cooling tube 128 (228) is connected to a supply of liquid nitrogen 150, and a temperature control 152 uses the measurements from the temperature sensors 130 (230) and 132 (232) to determine the amount of liquid nitrogen flowing through the cooling tube. The liquid nitrogen evaporated in this process is led off as waste gas via the line 154 (254).

The system illustrated in FIG. 2 operates as follows. The expirational respiratory gas from the anesthetic machine, first cleaned in the initial cleaning apparatus 10, is passed first of all via the pump controller and the pump 114 solely to one of the two deposition apparatuses, for example apparatus 120, with the outlet valve 124 of this apparatus remaining closed. On reaching the final pressure of 150 bar in the vessel of the deposition apparatus 120, the branch changeover unit 116 closes the inlet valve 122 and passes all further respiratory gas coming from the pump 114 to the other deposition apparatus 220. In the interim, the temperature controller 152 passes liquid nitrogen from the nitrogen reservoir 150 into the cooling tube 128, so that solid xenon is deposited on the cooling tube 128. When the xenon in the gas mixture has been substantially deposited, which can be ascertained, for example, by measuring when a characteristic time period has elapsed or by measuring the temperature pattern in the vessel of the deposition apparatus 120, the associated multiway valve 140 is set such that the gas coming from the outlet valve 124 is led off as waste gas, and the outlet valve 124 is opened. The overhead gas in the vessel, which contains the uncondensed components of the gas mixture introduced, is let off and led off as waste gas. The outlet valve 124 is subsequently closed and the vessel is heated by a heater (not shown) so that the xenon deposited on the cooling tube 128 is evaporated. In the course of this procedure a pressure of 65 bar is typically established within the vessel, corresponding to the pressure of customary commercial xenon bottles. After changeover of the multiway valve 140, the gaseous xenon thus obtained is then passed via the outlet valve 124 and the product line 141 to the pump 142, which passes the xenon to a downstream analysis stage or processing stage. After this, the deposition apparatus 120 is again ready to receive expirational respiratory gas from the pump 114. As soon as the maximum pressure of 150 bar is reached in the second deposition apparatus 220, into which all of the expirational respiratory gas produced in the interim has been pumped, the associated inlet valve 222 is closed and the pump 114 is reconnected, by means of the branch changeover unit 116, to the first deposition apparatus 120. The two deposition apparatuses 120 and 220 therefore operate in tandem, so that there is continuous processing of the expirational respiratory gas produced.

In this second embodiment of the novel recovery system, too, it is possible to provide modifications as in the case of the first embodiment described above. For example, here too the cooling tube 128 can be configured as a tube bundle. The product pump 142 may, depending on the nature of further processing, be omitted. Since the pressure of the vaporized xenon (typically 65 bar) corresponds to the pressure of customary commercial xenon bottles, the vessels of the deposition apparatuses 120 and 220 can also be used directly as compressed gas bottles. In this case provision can be made for the vessels to be changed after each recovery operation. It is of course also possible to employ more than two vessels, which are then successively filled or used for a recovery operation under direction by the branch changeover unit 116. Finally, it is also possible to couple two low-pressure systems as shown in FIG. 1, with the aid of a branch changeover unit, or to couple a low-pressure system with a high-pressure system, by way of a branch changeover unit, so that depending on requirements and circumstances it is possible to operate by the low-pressure process or the high-pressure process. Alternatively, it is also possible to use a single high-pressure deposition apparatus, for example the deposition apparatus designated as 120 in FIG. 2, and to provide—in a manner similar to the embodiment of FIG. 1—an intermediate store which accommodates the respiratory gas produced during the evaporation of the condensed xenon.

Since the recovered xenon is reused as anesthetic gas, the recovered xenon need not be of high purity. In accordance with the invention the recovered xenon is analyzed before the anesthetic gas is remixed and, if there are residual concentrations of oxygen and nitrogen, the corresponding proportion of oxygen or nitrogen which is added to the xenon when the anesthetic gas is remixed is reduced accordingly. Any other residual concentrations of impurities, for example $CO_2$, are physiologically unobjectionable and can, moreover, be taken into account accordingly, following an analysis of the recovered xenon, in the anesthesia supply.

What is claimed is:

1. A process for separating off xenon from a gas mixture, which comprises the following steps:
    a) flowing the gas mixture into contact with a cooling surface which is at a temperature below the melting point of xenon and under a pressure of from 0.6 to 150 bar,
    b) condensing in solid state a xenon component of the gas mixture on the cooling surface,
    c) removing away from the cooling surface those components of the gas mixture which are not condensed in solid state on the cooling surface, and
    d) liquefying the xenon component by heating the xenon component which has condensed on the cooling surface to above the melting point of xenon.

2. A process for separating off xenon from a gas mixture, which comprises the following steps:
    a) flowing the gas mixture into contact with a cooling surface which is at a temperature below the melting point of xenon and under a pressure of from 0.6 to 150 bar,
    b) condensing in solid state a xenon component of the gas mixture on the cooling surface,
    c) removing away from the cooling surface those components of the gas mixture which are not condensed in solid state on the cooling surface,
    d) heating the component which has condensed on the cooling surface to above the melting point of xenon, and
    e) performing steps a) and b) and c) and d) in at least two parallel deposition apparatuses wherein during the step of heating the condensed xenon in one deposition apparatus, the gas mixture produced is conveyed to one further deposition apparatus for condensing out the xenon to be separated.

3. A process for recycling an anesthetic gas whose components comprise xenon and one or more disposable gases, which comprises the following steps:

a. separating the xenon to be recovered from the contaminated gas mixture by a process for separating xenon from a gas mixture, which comprises the following steps:
  i flowing the gas mixture into contact with a cooling surface which is at a temperature below the melting point of xenon and under a pressure of from 0.6 to 150 bar,
  ii condensing in solid state a xenon component of the gas mixture on the cooling surface,
  iii removing away from the cooling surface those components of the gas mixture which are not condensed in solid state on the cooling surface,
  iv heating the xenon component which has condensed on the cooling surface to above the melting point of xenon, and
  v conveying the disposable gases together with the impurities away from the cooling surface following the condensation of the xenon to be recovered,
b) determining the residual content of the disposable gases in the recovered gas, and
c) remixing the gas mixture from the recovered gas while adding a proportion of fresh disposable gases, the amount of disposable gases added being determined as a function of the concentration of the disposable gases in the recovered gases.

4. The process as claimed in claim 3, wherein oxygen is a disposable gas.

5. A device for use in separating xenon from a gas mixture comprising:
  a deposition apparatus having a chamber for the passage of a gas mixture, said chamber having a cooling surface;
  a cooling apparatus thermally connected to said cooling surface for cooling said cooling surface to a temperature below the melting point of xenon; and
  a heater in thermal communication with said chamber for heating solid components which have condensed on said cooling surface; and said deposition apparatus having connecting structure for connecting said deposition apparatus to an anesthetic machine for separating off xenon from a gas mixture obtained in anesthesia from the anesthetic machine.

6. The device as claimed in claim 5, wherein said deposition apparatus includes a gas inlet communicating with said chamber and a gas outlet communicating with said chamber to create a path of flow of the gas through said chamber from said gas inlet to said gas outlet, and said cooling surface lying in the flow path of the gas.

7. The device as claimed in claim 6, wherein said deposition apparatus has a sealable vessel in which said chamber and said cooling surface and said heater are located.

8. The device as claimed in claim 7, including a pump operatively connected with said vessel for feeding the gas mixture into said vessel under pressure and outlet structure connected to said vessel for for discharging overhead gas from said vessel.

9. The device as claimed in claim 8, including at least one additional of said deposition apparatus, and a switchover device connected to each of said deposition apparatuses for passing the gas mixture alternatively into said deposition apparatuses.

10. The device as claimed in claim 5, including at least one additional of said deposition apparatus, and a switchover device connected to each of said deposition apparatuses for passing the gas mixture alternatively into said deposition apparatuses.

11. In an anesthetic machine the improvement being
  a) a recovering device for recovering xenon from a gas obtained in anesthesia, said recovering device having a deposition apparatus which includes a chamber for the passage of a gas mixture containing xenon, said chamber having a cooling surface, a cooling apparatus thermally connected to said cooling surface for cooling said cooling surface to a temperature below the melting point of xenon, and a heater thermally connected to said chamber for heating solid xenon components which have condensed on said cooling surface,
  b) a collection device, first conveying structure communicating with said collection device and said cooling surface for conveying the recovered xenon from said cooling surface to said collection device,
  c) an analysis device communicating with said collection device for analyzing the recovered xenon and
  d) a mixing device, second conveying structure communicating with said mixing device for conveying the recovered xenon and for conveying an anesthetic gas to said mixing device for remixing the anesthetic gas using the recovered xenon, which adjusts the mixing ratio as a function of the analytical result from the analysis device.

* * * * *